United States Patent [19]

Thornton et al.

[11] Patent Number: 5,129,789

[45] Date of Patent: Jul. 14, 1992

[54] MEANS AND METHOD OF PUMPING FLUIDS, PARTICULARLY BIOLOGICAL FLUIDS

[75] Inventors: Kenneth O. Thornton, Polk City; Steven J. Phillips, Des Moines, both of Iowa

[73] Assignee: Advanced Medical Systems, Inc., Polk City, Iowa

[21] Appl. No.: 512,821

[22] Filed: Apr. 23, 1990

[51] Int. Cl.⁵ .................... F04B 43/08; F04B 35/00
[52] U.S. Cl. ................................. 417/53; 417/322; 417/410; 600/16; 623/3
[58] Field of Search .............. 417/322, 410, 53; 600/16; 604/151; 623/3

[56] References Cited

U.S. PATENT DOCUMENTS

| 3,370,538 | 2/1968 | Hines | 417/322 |
|---|---|---|---|
| 3,406,670 | 10/1968 | Hines | 417/322 X |
| 3,924,974 | 12/1975 | Fishbeck et al. | 417/322 |
| 4,519,751 | 5/1985 | Beckman et al. | 417/322 |
| 4,726,741 | 2/1988 | Cusack | 417/410 X |
| 4,731,076 | 3/1988 | Noon et al. | 417/322 X |
| 4,795,317 | 1/1989 | Cusack | 417/410 X |
| 4,795,318 | 1/1989 | Cusack | 417/410 X |
| 4,804,314 | 2/1989 | Cusack | 417/322 |
| 4,815,946 | 3/1989 | Cusack | 417/410 X |
| 4,917,579 | 4/1990 | Torma | 417/332 |

FOREIGN PATENT DOCUMENTS

| 60-17279 | 1/1985 | Japan | 417/322 |
|---|---|---|---|
| 628329 | 10/1978 | U.S.S.R. | |
| 783919 | 11/1980 | U.S.S.R. | 417/410 |
| 1043342 | 9/1983 | U.S.S.R. | |
| 1341381 | 9/1987 | U.S.S.R. | 417/322 |

Primary Examiner—Gerald A. Michalsky
Attorney, Agent, or Firm—Zarley, McKee, Thomte, Voorhees & Sease

[57] ABSTRACT

A system for pumping of fluids, particularly biological fluids such as blood, including a tubular length of magnetostrictive material. One-way valves are positioned generally in opposite ends of the tubular material. Fluid flow conduits are connected to the opposite ends of the tubular material. A magnetic field is imposed, generally by an electric coil, in a pulsed fashion to the tubular material to cause alternatingly magnetostriction and relaxation of the tubular material. This causes a reciprocating variation in the distance between the one-way valves which oppositely are opened and closed to produce a pumping action through the tubular material.

5 Claims, 3 Drawing Sheets

MEANS AND METHOD OF PUMPING FLUIDS, PARTICULARLY BIOLOGICAL FLUIDS

BACKGROUND OF THE INVENTION

A. Field of the Invention

The present invention relates to pumping fluids, particularly biological fluids such as blood. In particular, the invention relates to a means and method for producing low power, reliable, nonturbulent pumping of biological fluids through a fluid circuit.

B. Problems in the Art

A variety of conventional ways exist to pump fluid. As is well known in the art, various pumps exist in a variety of different forms for a variety of different purposes. Two examples of conventional pumps often used with biological fluids are peristaltic and centrifugal pumps.

Certain conventional pumps have advantages and disadvantages over other types. Generally, however, all conventional fluid pumps when used with biological fluids and particularly blood, have one or more of the following problems:

(1) many utilize substantial amounts of power to operate;
(2) some require conversion between several forms of energy to ultimately produce pumping of the fluid;
(3) many are inefficient or do not retain their efficiency over various flow rates or through-puts;
(4) many damage or otherwise work trauma on the cells of biological fluids being pumped;
(5) many create turbulence which in turn creates a turbulent flow through the fluid circuit.

Furthermore, many pumps, even when used for pumping relatively small amounts of fluids, are bulky, large, and/or noisy or vibratory.

It is therefore a principle object of the present invention to present a means and method of pumping fluids, particularly biological fluids such as blood, which improves over or solves the problems and deficiencies in the art.

It is a further object of the present invention to present a means and method as above described which utilizes relatively little amount of energy to operate.

A still further object of the present invention is to provide the means and method as above described which minimizes contact with, as well as trauma and damage to, the fluid being pumped.

A further object of the present invention is to provide a means and method as above described which is simple in construction, reliable, and durable.

A still further object of the present invention is to provide a means and method as above described which utilizes a direct transfer of mechanical energy to the fluid being pumped.

Another object of the present invention is to provide a means and method as above described which utilizes accelerative and inertial pumping of the fluid to produce a smooth, continuous laminar flow of fluid.

These and other objects, features, and advantages of the present invention will become more apparent with reference to the accompanying specification and claims.

SUMMARY OF THE INVENTION

The present invention relates to a means and method for pumping fluids, particularly biological fluids such as blood, which utilizes the unique technique of passing either the fluid or its fluid conduit through a bore in a length of magnetostrictive material. The material can operate alone or at least one-way fluid flow restrictive means is positioned in the fluid path through the bore in the magnetostrictive tube. A magnetic field is imposed upon the magnetostrictive material in periodic pulses.

The magnetostrictive material responds by alternatingly reciprocating synchronously with the pulses between a magnetostricted state and a relaxed original state. The material changes dimensions with each pulse and relaxation and causes fluid displacement. Movement and pressure of incoming fluid on the one-way flow restriction means, if used, allows successive volumes of fluid into the bore of the magnetostrictive tube. A second one-way flow restriction means can be used at the opposite end of the bore, and resists flow in variance to the first one-way flow resistor means, allowing fluid which presses against it to exit to an outlet conduit.

This reciprocating action creates displacement, and thus pumping of the fluid. The pulsing of the magnetic field is generally very fast which creates accelerative and inertial-type flow as the magnetostrictive material expands and relaxes many times a second allowing smooth, continuous, non-turbulent fluid flow.

The rate of magnetic field pulsation can be controlled for different fluid flow rates. Other optional features can be incorporated. For example, a permanent magnet or a biasing circuit can be used to enhance magnetostriction by biasing the magnetic field which affects the way the material magnetostricts; or a casing could surround the coil and magnetostrictive material for purposes of compression of the material and/or for shielding and protection, such as is desired.

The pump represents a means and method for producing a reliable, non-turbulent laminar fluid flow pumping action using low power consumption and with a non-complex construction. The pump is significantly less damaging to the fluid.

DETAILED DESCRIPTION OF THE PREFERRED EMBODIMENT

Figure 1:
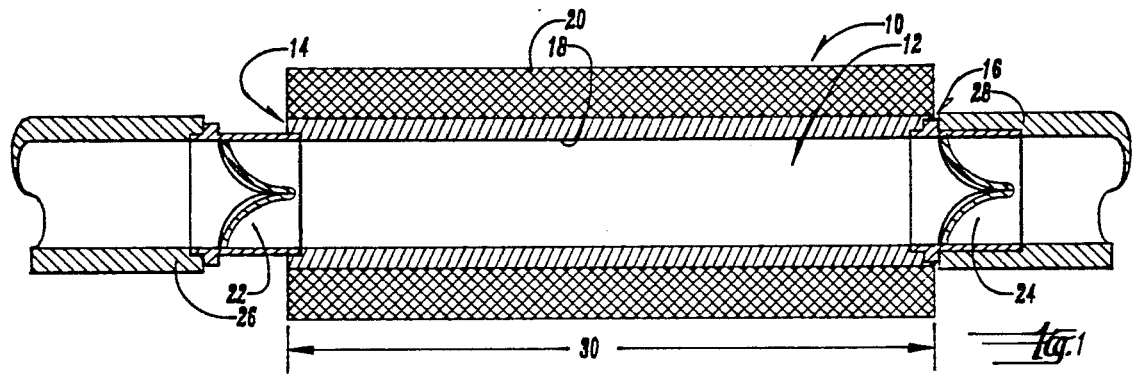
FIG. 1 is a simplified sectional schematic diagram of a fluid pump according to the present invention.

With specific reference to the drawings, a preferred embodiment of the present invention will now be described. It is to be understood that this preferred embodiment relates to the pumping of blood for a human patient for which the pump described herein is especially adapted. Certain specifics regarding this use will be explained in detail to illustrate the advantages of the present invention in comparison to conventionally used means and methods. However, the invention may also have uses for other fluid pumping applications. The description of this preferred embodiment does not nor is it intended to specifically limit the scope of the invention.

Reference numerals are used to identify elements or locations in the drawings. The same reference numerals will be used for the same elements or locations in all the drawings unless otherwise indicated.

The basic simplified structure of a magnetostrictive fluid pump (referred to generally by reference numeral 10) can be seen at FIG. 1. Pump 10 includes a tubular section 12 of magnetostrictive material having opposite open ends 14 and 16 and a central bore 18 substantially encased by an electrical coil 20 to create a magnetic field around and through section 12.

First and second one-way valves 22 and 24 are positioned and secured respectively in open ends 14 and 16 by means known within the art. Valve 22 is at the open inlet end 14 whereas valve 24 is at the open outlet end 16 of tubular section 12. As shown, inlet and outlet conduits 26 and 28 are also sealingly attached into ends 14 and 16 respectively.

The properties of rare earth magnetostrictive material are known in the art. See, for example, A.E. Clark, "Introduction to Highly Magnetostrictive Rare-Earth-Materials", U.S. Navy Journal of Underwater Acoustics, 27, 109–125 (1977); A.E. Clark & D.N. Crowder, "High Temperature Magnetostriction of $TbFe_2$ and $Tb_{.27}Oy_{.73}Fe_2$", Trans. Mag., MAG-21, No. 5 (1985); R.W. Timme, "Magnetomechanical Characteristics of Terbium-Holmium-Iron Alloy," J. Acoust. Soc. Am., 59, 459–464 (1976); "Proceedings of the First International Conference on Giant Magnetostrictive Alloys and Their Impact on Actuator and Sensor Technology," Marbella Spain, Carl Tyren, Ed., Fotynova, Lund Sweden (March 1986).

The properties of magnetostrictive materials are such that an imposition of a magnetic field upon the material causes it to change size. In fact, the material can be produced so that it can have directional expansion. Magnetostriction is defined as the change of length of a ferromagnetic substance when it is magnetized. More generally, magnetostriction is the phenomenon that the state of strain of a ferromagnetic sample depends on the direction and extent of magnetization.

In the preferred embodiment of the invention, tubular section 12 is made from a material designated as ETREMA Terfenol-D ®, which can be pre-processed to expand directionally in the presence of a magnetic field. This material is publicly available through Edge Technologies of Ames, Iowa. Terfenol is the binary rare earth iron alloy $TbFe_2$. ETREMA Terfenol-D ® is an alloy of the form $Tb_xDy_{1-x}Fe_{1.9-2}$. Directionally, solidified compositions can be produced by a freestand zone melt (FSZM) or a modified Bridgman (MB) method.

In particular, in the presence of a magnetic field the tubular section 12 expands. As can be appreciated, lengthening of section 12 longitudinally results in shrinkage laterally; similarly to a rubber band which is stretched along its length. As can be understood by referring to FIG. 1, such expansion causes the distance 30 (between opposite open ends 14 and 16) to increase which in turn causes the distance between valves 22 and 24 to increase, as they are fixed to section 12.

The distance designated by reference numeral 30, in the preferred embodiment shown in FIG. 1, changes approximately 1/1000th of an inch per inch of tubular section 12 at a 10 megacycle pulsing of coil 20. It is to be understood that section 12 would increase in length approximately twice as much as the bore 18 would be narrowed by the stretching expansion of tubular section 12. Thus, the interior volume of bore 18 increases upon magnetostriction and valves 22 and 24 move farther apart. This very high speed reciprocation results in the first one-way valve 22 opening and closing approximately at the same frequency. Because of these many but small movements of valve 22 along the fluid flow line, small amounts of fluid in inlet conduit 26 will pass through valve 22, each time it opens, into bore 18. As these small volumes of fluid enter bore 18, fluid pressure builds up and then causes a like amount of fluid to exit out of alternatingly opening and closing second one-way valve 24 at the outlet end 16 of tubular section 12. Thus, this structurally non-complex configuration operates at a high enough rate to pump fluid both through the pump itself as well as through a fluid circuit.

As can further be appreciated, the size and length of tubular section 12 can be varied for different uses, as can the size, strength, and level of the magnetic field created by coil 20.

Figure 2:
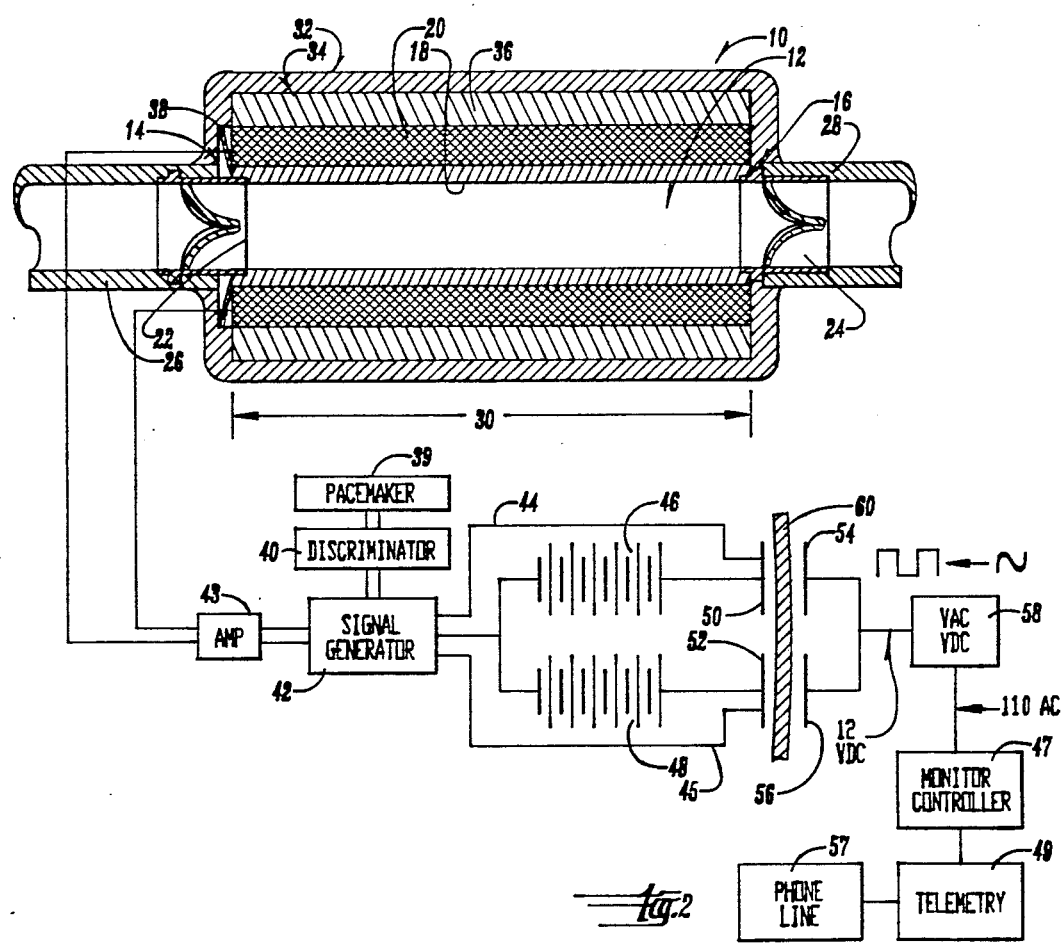
FIG. 2 is a partial sectional, partial schematic diagram showing an embodiment of a pumping system according to the invention.

FIG. 2 depicts schematically a specific application of pump 10 of FIG. 1. In this preferred embodiment, tubular section 12 is four inches long in its relaxed normal condition. The inside diameter of bore 18 is 14 millimeters. Coil 20 is an 8 ohm coil. Valves 22 and 24 are preferably Kolff tri-leaf polyurethane "Utah" valves (see FIGS. 7–10).

In this embodiment, pump 10 can be placed inside or outside a patient and used as a total artificial heart, replacing the pumping function of the biological heart, or it can be used outside the patient as a ventricular assist device. Either way, inlet and outlet conduits 26 and 28 would be connected to the circulatory system of a patient, such as is known in the art.

A specific problem involved in utilizing pump 10 in this capacity is to insure that all surfaces of the pump, which either might come in contact with the patient's tissues, fluids, or blood, are bio-compatible. Therefore, conduits 26 and 28 are made from known-in-the-art bio-compatible materials (i.e. silicone-elastic available under the trademark Silastic ™ from Dow-Corning, or certain types of medically-approved polyurethane). Tubular member 18 is itself bio-compatible. Additionally, a shield 32 covers the entire pump 10, including the end surfaces. In the preferred embodiment, shield 32 is made of a bio-compatible substance and sealingly encapsulates pump 10. It is to be understood that shield 32 can also function in at least two other capacities.

First, it can be made of materials which will shield pump 10 from external magnetic fields as well as from fluids or other substances. Secondly, it can be made of a material which can hold tubular member 18 laterally in compression. It is to be understood that Terfenol-D can exhibit more pronounced magnetostriction under compression. FIG. 2 depicts a spring 38, which is positioned in a gap between tubular member 18 and shield 32 on the left-hand side of FIG. 2. This allows longitudinal expansion while member 18 is kept in compression along its length.

FIG. 2 also shows that an intermediary sleeve 34, comprising a permanent magnet, could be positioned between shield 32 and coil 20 (see reference numeral 36). Such a sleeve could bias the magnetic field of the coil to achieve desired effects on magnetostriction of member 18.

As can be understood, conduits 26 and 28 can be directly attached into the patient's circulation system if used as an artificial heart.

Coil 20 is powered by signal generator 42 which produces a frequency or pulsed signal based on a pacemaker 39 (such as is known in the art). A discriminator means 40 could be inserted between pacemaker 39 and generator 42 to assist in making sure the pace (heart rate) signal sent to generator 42 is correct. Amplifier 43 takes the signal from generator 42 and provides a pulsed direct current at a selected frequency to energize and de-energize coil 20 to cause the reciprocation and pumping action of pump 10.

The preferred embodiment of FIG. 2 also schematically illustrates that a power source for generator 42 can be batteries 46 and 48. Still further, these batteries can be rechargeable such as is known in the art.

As a further option to the embodiment if the system is, for example, inserted inside the patient and there is no direct way to connect recharging power, the batteries can be rechargeable by using an inductive plate arrangement having inductive plates 50 and 52 each connected to a battery 46 and 48, and inductive plates 54 and 56 connected to an electrical power recharging source 58. Plates 50, 52 and 54, 56 do not need to come into direct contact to accomplish recharging. Electrical recharging power can be transmitted even through a sheet or wall (such as skin 60) of material by utilizing the inductive properties of this arrangement. Inductive plates 50 and 52 could be positioned inside the body at a known location. Skin 60 (and perhaps other tissue) would then separate plates 50 and 52 from exterior environment. Recharging could be accomplished, by positioning plates 54 and 56 at an appropriate position across from plates 50 and 52. The ability to pass electricity between the plates is not unlike the inductive plate technology utilized with regard to automobile antennas which are positioned on the car's windshield and transmit their signal through the windshield glass without any direct hard-wired connection through the glass.

FIG. 2 schematically depicts additional options. Wires 44 and 45 can be connected from plates 50 and 52 to generator 42, or any other component. By use of a monitor/controller 47, signals could be sent through the inductive plates to do such things as change the rate of pacemaker 39. Conversely, information could be received by monitor/controller 47 from the internal components, such as generator 42 so its generation could be checked and recorded.

Still further, a telemetry device 47 and/or phone line 51 could optionally be used to allow communication of monitor (controller to a remote location). A hospital, for example, could monitor the patient from afar, and could even change the pacemaker functioning, if desired or needed.

FIGS. 3, 4, 5 and 6 depict diagrammatically how pump 10 accomplishes the pumping of fluid. It is to be understood that the dimensions of these figures is greatly exaggerated to illustrate the principles involved.

Figure 3:
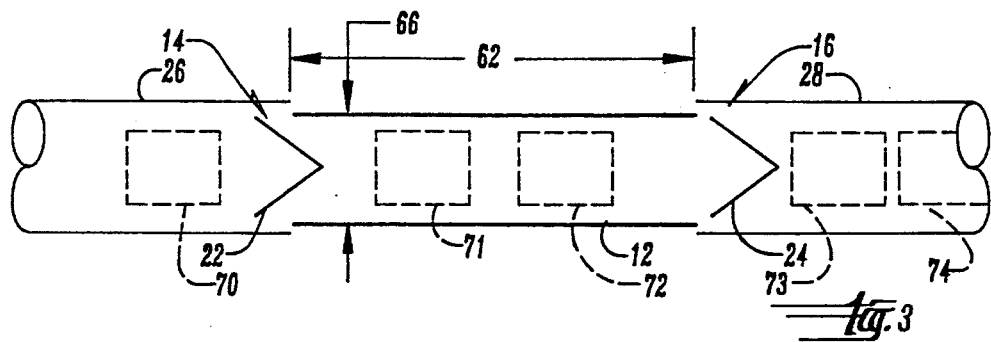
FIG. 3, 4, 5 and 6 are schematic diagrams of pumping action created by the pump of FIG. 1.

FIG. 3 shows tubular section 12 and one-way valves 22 and 24 in what will be called a relaxed or normal position. Tubular section 12 has a length designated by reference numeral 62 between ends 14 and 16. Both valves 22 and 24 are in a closed position.

The pump is self-priming in the sense that once pulsed current is sent to a coil surrounding tubular conduit 26, the magnetostriction of section 12 begins, varying the distance between valves 22 and 24, and setting the accelerative and inertial flow of fluid through the pump in motion.

Any fluid which is at open inlet end 14 would present pressure on valve 22. Thus, when tubular section 12 is in its relaxed length 62, shown in FIG. 3, the fluid pressure on the left-hand side of the valve 22 is waiting to cause the leafs to move apart and allow fluid into bore 18 of tubular section 12. Fluid first needs to fill up the volume of bore 18 over successive repeated expansions. Because there would be no significant fluid pressure on the inlet side of opposite fluid valve 24 as of yet, it would remain closed and allow bore 18 to fill up with fluid.

Figure 4:
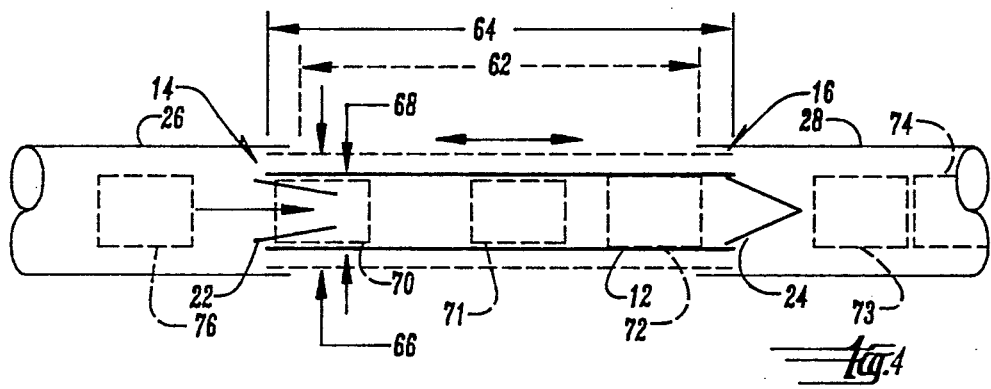

Once, however, bore 18 is filled up, the fluid flow begins through valve 24. Every time tubular section 12 expands magnetostrictively to length 64 as shown in FIG. 4, the lower pressure of fluid within bore 18 against the right-hand side of valve 22 causes it to remain closed. This prevents any fluid from back-flushing into bore 18 from outlet conduit 28. This also means that the narrowing of bore would actually allow valve 22 to open and allow fluid to fill into bore 18. The volume or block of blood designated at reference numeral 70 would move into bore 18.

Figure 5:
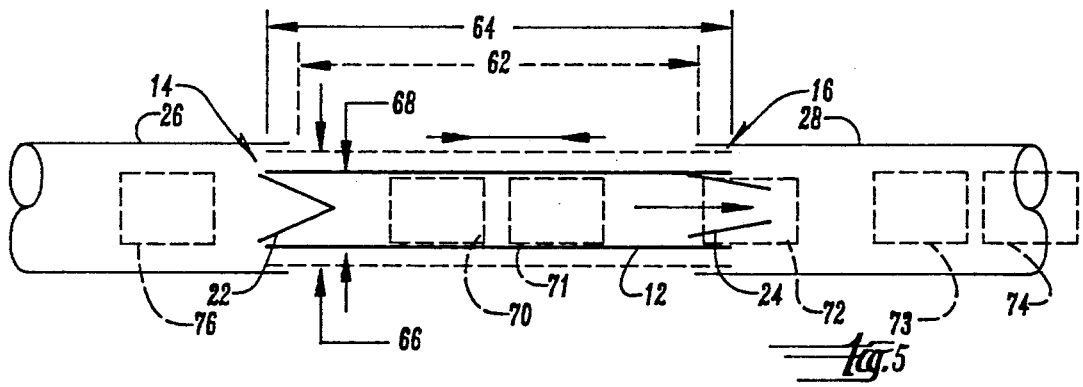

Next, as shown in FIG. 5, de-energization of the coil would cause tube 12 to start to move back to its retracted relaxed position. Valve 22 closes because of back pressure from fluid in filled bore 18, and accelerates by pushing fluid inside bore 18. The path of least resistance for the volume of fluid within bore 18 would be through valve 24.

As is shown by the double-ended arrow in FIG. 4, tubular section 12 is expanding to its magnetostricted state. New length 64 is longer than length 62 (shown in ghost lines), generally by 4/1000th of an inch (1/1000th inch per inch of each of the four inch length of tubular section 12). Additionally, diameter 66 in FIG. 3 is reduced to a diameter 68 in FIG. 4. This moves valves 22 and 24 away from each other.

FIG. 5 shows tubular section 12 as it begins returning or retracting to its relaxed position (see the double-ended arrow). This means section 12 returns to length 62 and diameter 68. Valves 22 and 24 move towards each other. Blood block 72 is pushed through the open valve 24 to outlet port 28, while the back pressure on valve 22 keeps it in a closed position. This prevents reflux or back-flushing of the fluid back into inlet conduit 26.

Figure 6:
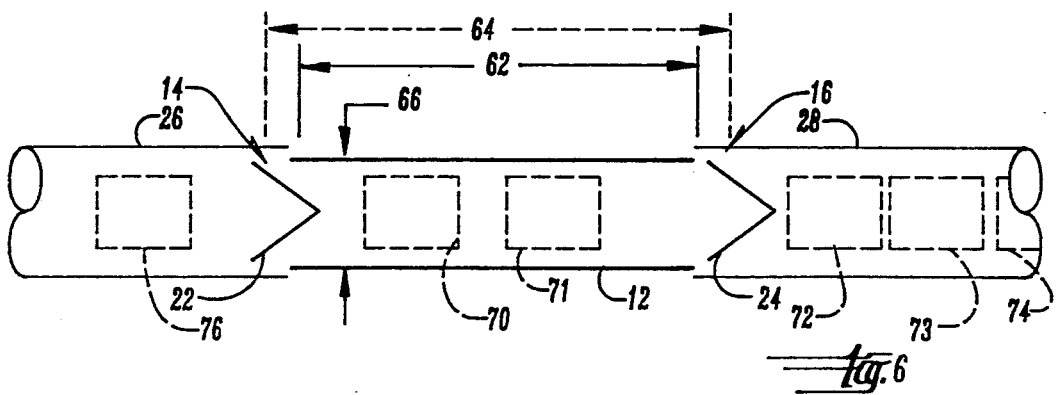

FIG. 6 illustrates section 12 at its relaxed length following movement started in FIG. 5. It will immediately begin to move to its expanded magnetostricted state (see FIG. 4) where valve 22 again allows blood to fill into bore 18, at the same time causing valve 24 to close to prevent back-flush. This pumping action continues at a frequency set by generator 42.

The accelerative inertia and movement of fluid through tubular section 12 can be visualized by referring to dashed boxes 70, 71, 72, 73, 74, and 76 in FIGS. 3-6. Each represents approximately equivalent volumes or blocks of fluid. As section 12 expands and constricts in FIG. 4, open valve 22 allows block 70 through. As section 12 relaxes in FIG. 5, closed valve 22 pushes and accelerates blocks 70, 71, 72, to pump block 72 out valve 24 and prevents back-up of block 70 into inlet 26. Once started, flow continues smoothly.

Generally this is somewhere in the range of 70-90 cycles a second. If coil 20 is an 8 ohm coil, this results in approximately 2 watts of electrical power being used per day of operation. Such low power consumption is extremely advantageous and allows the use of batteries for power.

Figure 7:
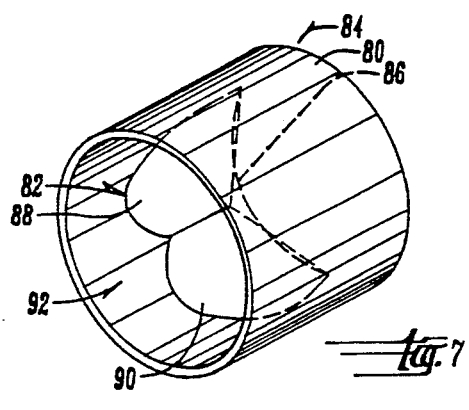
FIGS. 7, 8, 9 and 10 are various views of a one-way valve according to the preferred embodiment of the invention.
Figure 8:
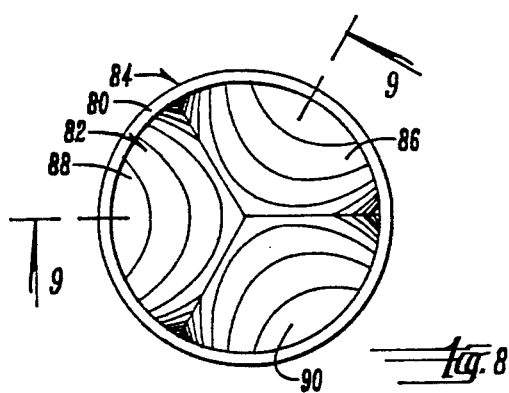

FIGS. 7, 8, 9, and 10 show the preferred embodiment for valves 22 and 24 (called Utah or Kolff tri-leaf valves). An annular casing 80 encloses the tri-leaf configuration for one-way valve 84. Each leaf 86, 88 and 90 is in a normally closed position as shown in FIGS. 7 and 8. Depending on the direction it is positioned within the fluid flow conduit, it disallows fluid flow in the right-to-left direction of FIG. 9.

Figure 9:
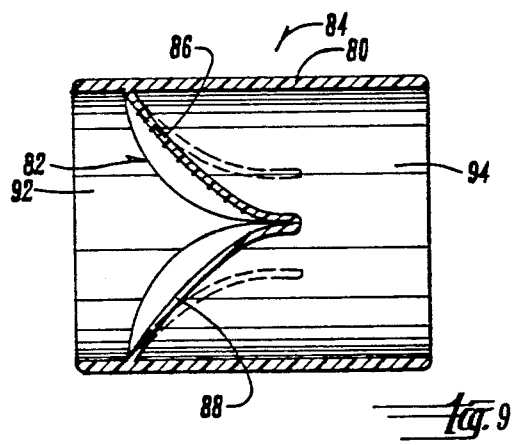
Figure 10:
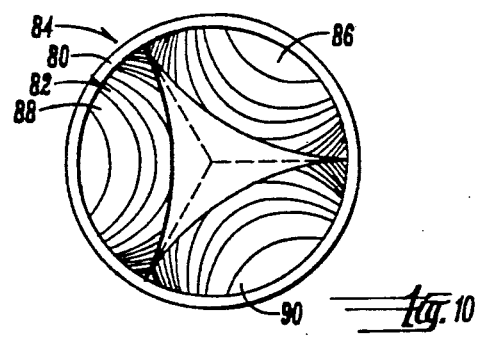

By referring to FIG. 9, it can be seen that when the pressure on leafs 86, 88, and 90 is greater on side 92, the valve will remain closed. However, when pressure on side 94 exceeds that on side 92, the leafs will spread at their center, as shown by dashed lines 96 in FIG. 9, and as shown in solid lines in FIG. 10, allowing fluid to flow only in a left-to-right direction in FIG. 9.

It can be seen that in actual operation this pumping means and method is especially suitable for pumping blood without damage to the cells. The pumping action is gentle, does not create turbulence and the flow of blood is laminar. In addition, the contact between the mechanical elements of the pump and the blood is essentially eliminated. In other words, the blood contacts only biocompatible materials and avoids all contact with any hard, metallic pump or valve parts. At the same time, the dwell time inside of the pump is extremely short. As a result of these unique features there is little opportunity for damage to the blood cells as typically occurs in peristaltic, centrifugal, diaphragm or balloon action pumps.

Other mechanical advantages include simplicity of elements which means less opportunity for mechanical failures, the ability to run on small power sources, portability, and ease of operation. All of these unique advantages offer great opportunities for use in blood pumping either for heart replacement or ventricular assist. Also, its small site allows it to be placed right in the circulation system, or at least very close to it. This eliminates the long tubing lines of other systems and significantly cuts down on hemolysis due to friction along the lines.

The preferred embodiment is given by way of example only, and not by way of limitation to the invention, which is solely described by the claims herein. Variations obvious to one skilled in the art will be included within the invention defined by the claims.

For example, pump 10 can be utilized for pumping all types of fluids and for all types of applications. It is not restricted to use as an artificial heart or as a ventricular assist device.

Additionally, there are different types of magnetostrictive materials other than Terfenol-D which can work according to the invention. Likewise there are different types, sizes, and specifications for coil 20. There are even alternative ways to present and bias the magnetic field to the magnetostrictive material.

Also, different control circuitry and power sources could be adapted for use with the device. Other springs and/or compression combinations can be used, as well as different ways of biasing the coil, such as a circuit connected to the coil with appropriate elements. The magnetic biasing can be used to spread out the magnetic field of the coil so it is uniform along the coil and not concentrated in certain areas.

It is to be understood that one-way fluid flow restrictors could be substituted for one-way valves. For example, a helical member inserted in bore 18 could offer greater resistance to fluid flow in one direction than the other. Additionally, the invention could operate with only one one-way valve or one one-way flow restrictor.

Furthermore, one-way valves or flow restriction means may not even have to be used. The magnetostriction causing fluid displacement by itself and therefore can pump fluid alone if desired.

What is claimed is:

1. A method of pumping useable blood comprising:
   connecting a useable blood inlet conduit and a useable blood outlet conduit to a length of magnetostrictive tubing having a longitudinal axis;
   keeping the length of magnetostrictive tubing under compression along its longitudinal axis; and
   imposing a pulsed electromagnetic field on the tubing to cause magnetostriction of the tubing and blood displacement in one direction.

2. The method of claim 2 wherein the electromagnetic field is pulsed by a DC power source.

3. The method of claim 1 further comprising the step of controlling the amplitude of the pulsed electromagnetic field.

4. The method of claim 1 further comprising the step of controlling the frequency of the pulsed magnetic field.

5. The method of claim 5 wherein a permanent magnet is utilized when generating the pulsed electromagnetic field.

* * * * *